(12) United States Patent
Fink et al.

(10) Patent No.: US 7,988,923 B2
(45) Date of Patent: Aug. 2, 2011

(54) DEVICE, SYSTEM AND METHOD FOR AN ADVANCED OXIDATION PROCESS USING PHOTOHYDROIONIZATION

(75) Inventors: Ronald G. Fink, Jupiter, FL (US); Walter B. Ellis, Jupiter, FL (US)

(73) Assignee: RGF Environmental Group, Inc., West Palm Beach, FL (US)

( * ) Notice: Subject to any disclaimer, the term of this patent is extended or adjusted under 35 U.S.C. 154(b) by 1479 days.

(21) Appl. No.: 10/784,867

(22) Filed: Feb. 23, 2004

(65) Prior Publication Data

US 2005/0186124 A1 Aug. 25, 2005

(51) Int. Cl.
*B01J 19/08* (2006.01)
(52) U.S. Cl. ..................... 422/186.3; 422/121
(58) Field of Classification Search ............... 422/186.3, 422/121
See application file for complete search history.

(56) References Cited

U.S. PATENT DOCUMENTS

| | | | | |
|---|---|---|---|---|
| 4,892,712 | A * | 1/1990 | Robertson et al. | 422/186 |
| 5,933,702 | A * | 8/1999 | Goswami | 422/186.3 |
| 6,053,968 | A * | 4/2000 | Miller | 96/224 |
| 6,063,343 | A * | 5/2000 | Say et al. | 422/186.3 |
| 6,238,631 | B1 * | 5/2001 | Ogata et al. | 422/186.3 |
| 6,315,963 | B1 * | 11/2001 | Speer | 422/186.3 |
| 6,403,033 | B1 | 6/2002 | Gutman | |
| 6,972,415 | B2 * | 12/2005 | Schaible et al. | 250/436 |
| 2002/0155027 | A1 | 10/2002 | Gutman | |
| 2005/0008549 | A1 * | 1/2005 | Hsu | 422/186 |

FOREIGN PATENT DOCUMENTS

WO WO 02/102497 A1 * 12/2002

OTHER PUBLICATIONS

Press Release, "RGF's PHI-Cell," Sep. 15, 2003, RGF Environmental Group, Inc.

* cited by examiner

*Primary Examiner* — Kishor Mayekar
(74) *Attorney, Agent, or Firm* — Rothwell, Figg, Ernst & Manbeck, P.C.

(57) ABSTRACT

A device, system, and method, for the formation of advanced oxidation products by contacting a hydrated catalytic surface of a catalytic target structure with broad spectrum ultraviolet light in the 100 nm to 300 nm range that preferably includes 185 nm and 254 nm wavelengths. The catalytic surface reacts with the ultraviolet light energy and hydrate at the catalytic surface to form advanced oxidation products. The catalytic surface in one embodiment includes a hydrophilic agent, titanium dioxide, silver, copper, and rhodium. Preferably, the catalytic surface is coated with a coating that includes the hydrophilic agent, titanium dioxide, silver, copper, and rhodium. A photohydroionization cell (100) that includes an ultraviolet light source (204) and a catalytic target structure (110) in an air environment to form advanced oxidation product is also provided. A U.V. light indicator and a monitor and/or control system for the photohydroionization cell (100) are also provided.

24 Claims, 7 Drawing Sheets

BROAD SPECTRUM UV EMITTED FROM CELL 185 nm produces ozone

Ozonide Ions
Hydro-peroxides
Hydroxides
Super Oxide Ions

ODORS, MOLD
BACTERIA
VIRUS, VOCs

DEVICE, SYSTEM AND METHOD FOR AN ADVANCED OXIDATION PROCESS USING PHOTOHYDROIONIZATION

BACKGROUND OF THE INVENTION

1. Field of the Invention

The present invention generally relates to the field of applying ultraviolet light to an environment to create oxidizing agents for killing microbes, such as bacteria, mold, and viruses, and for destroying odors, and more particularly to an advanced oxidation process utilizing ultraviolet light to provide advanced oxidation product to an environment.

2. Description of Related Art

Oxidation is a chemical reaction in which an element or ion is increased in positive valence, losing electrons to an oxidizing agent. To oxidize is to change a substance by chemical reaction by combining it with oxygen such as by fire or rust. Oxidation processes can be used to kill bacteria, mold, and viruses. They are also routinely used to react with odor causing chemicals, such as volatile organic compounds, and other inorganic and organic chemicals.

Germicidal ultraviolet light rays (254 nm) have been used for inactivating microorganisms such as germs, viruses and bacteria. Ultraviolet light is dependable and can be easily installed. Germicidal ultraviolet light, however, is effective in reducing only the airborne microorganisms that pass directly through the light rays. Germicidal ultraviolet light, unfortunately, has little to no effect on gasses, vapors, or odors.

While ultraviolet light energy (185 nm) can, when applied to air in an environment, create ozone gas, and ozone is a strong oxidizer, ozone in elevated quantities can be toxic to humans and animals as well as can have undesired reactions to an environment.

Therefore a need exists to overcome the problems discussed above, and in particular, to provide a device, system, and method for a significantly improved oxidizing process to reduce microbes and odors in an environment.

SUMMARY OF THE INVENTION

According alternative preferred embodiments of the present invention, advanced oxidation products, such as Hydroxyl Radicals, Ozone, Hydroperoxide radicals, Ozonide ions, Hydroxides, and Super Oxide ions, Hydrogen Peroxide can be formed by a new and novel device, system, and method. These advanced oxidation products comprise strong and effective oxidizers that react with undesired compounds in an environment such as microbes, odor-causing chemicals, and other inorganic and organic chemicals, to destroy and/or inactivate such undesired compounds.

In accordance with a preferred embodiment of the present invention, a device comprises: an ultraviolet light source for emitting ultraviolet light, the ultraviolet light emitted from the ultraviolet light source including ultraviolet light energy at about 100 nm and at about 300 nm; and a catalytic target structure, mechanically coupled to the ultraviolet light source and including a surface, the surface of the catalytic target structure comprising titanium dioxide and at least one of the following metallic compounds: silver; copper; and rhodium, and wherein the surface of the catalytic target structure after contact with ultraviolet light reacts with hydrate at the surface to form advanced oxidation product.

The catalytic surface of the catalytic target structure preferably comprises titanium dioxide, silver, copper, and rhodium. Additionally, according to an alternative preferred embodiment, the catalytic surface comprises a hydrating agent (hydrophilic compound) as well as titanium dioxide, silver, copper, and rhodium. The hydrating agent may include water, moisture, and/or humidity at the catalytic surface, while the hydrophilic agent may comprise Silica Gel, Calcium Chloride, Sodium Choride, or other known agents with hydrophilic properties.

According to an alternative preferred embodiment, the catalytic surface is designed for maximum surface contact with the ultraviolet light. Preferably, the surface comprises a ridged or pleated design.

According to a preferred embodiment, a photohydroionization cell includes a catalytic target structure substantially surrounding an ultraviolet light source. The new and novel photohydroionization cell can effectively form advanced oxidation product for an advanced oxidation process.

In accordance with an alternative preferred embodiment of the present invention, a system for the formation of advanced oxidation product comprises: at least one ultraviolet light source for emitting ultraviolet light, the ultraviolet light emitted from at least one ultraviolet light source including ultraviolet light energy at about 100 nm and at about 300 nm; and at least one catalytic target structure including a surface for contact by ultraviolet light from at least one ultraviolet light source, the surface of at least one catalytic target structure comprising titanium dioxide and at least one of the following metallic compounds (preferably all three): silver; copper; and rhodium, and wherein the surface of the at least one catalytic target structure after contact with ultraviolet light reacts with hydrate at the surface to form advanced oxidation product. In an alternative embodiment, the system includes a plurality of ultraviolet light sources and a plurality of catalytic target structures.

A new and novel coating for a surface of a catalytic target structure preferably comprises various combinations of the following: a hydrophilic agent, titanium dioxide, silver, copper, and rhodium, such that the catalytic target structure with the coating at the surface will be useful for forming advanced oxidation product according to alternative preferred embodiments of the present invention.

A new and novel method for forming advanced oxidation product according to an alternative embodiment of the present invention is also provided. The method preferably comprises: hydrating a catalytic surface, the catalytic surface comprising titanium dioxide and the following metallic compounds: silver, copper, and rhodium; contacting the catalytic surface with ultraviolet light; and forming advanced oxidation product at the catalytic surface. The method can optionally include hydrophilically absorbing hydrate from an atmosphere surrounding the catalytic surface.

BRIEF DESCRIPTION OF THE DRAWINGS

The features and advantages of the present invention will be made apparent by the following detailed description of an embodiment thereof, provided merely by way of non-limitative example, which will be made in connection with the attached drawings, wherein.

DESCRIPTION OF THE PREFERRED EMBODIMENTS

Figure 1:
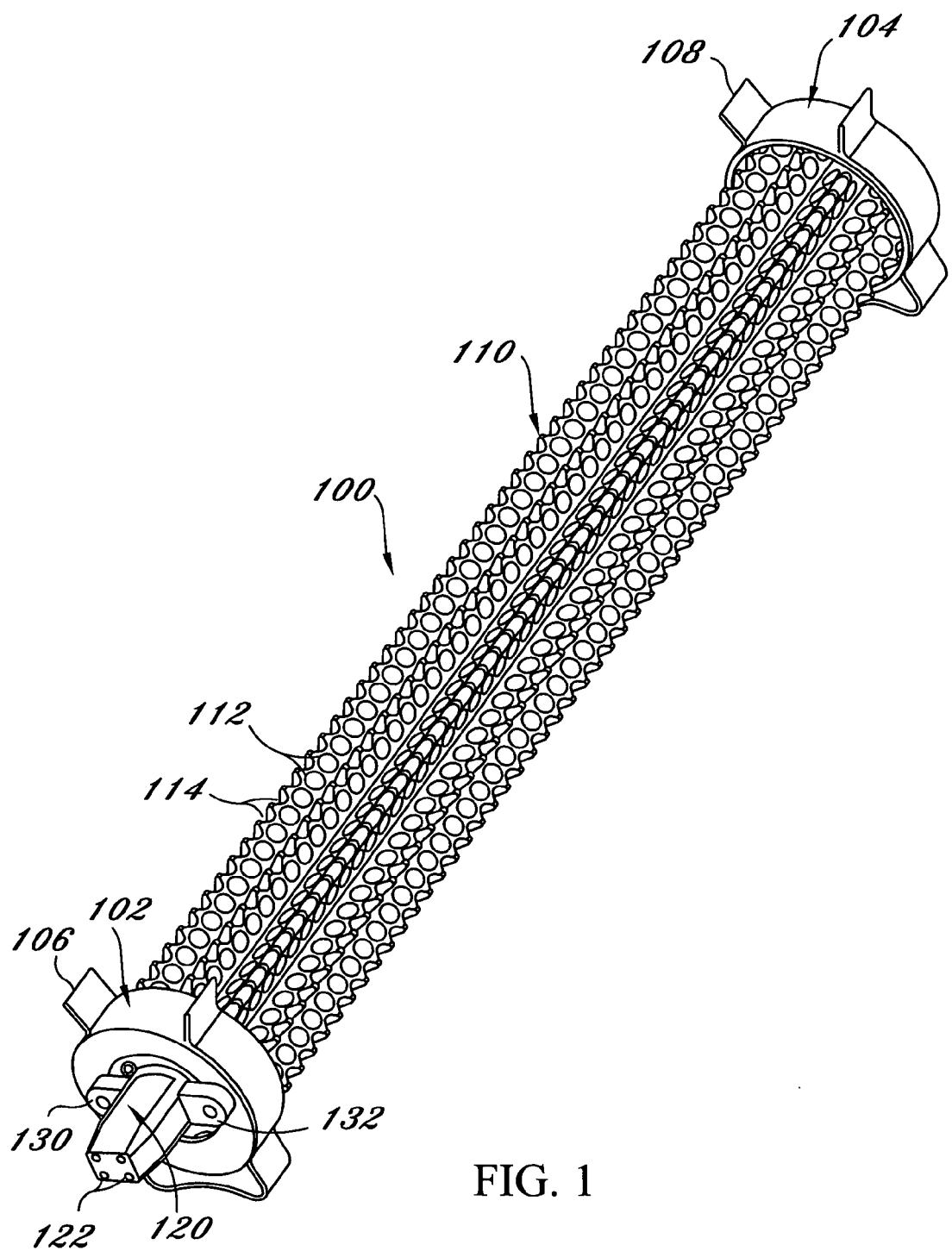
FIG. 1 is a perspective view of a PHI Cell according to a preferred embodiment of the present invention.

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting; but rather, to provide an understandable description of the invention.

The terms "a" or "an", as used herein, are defined as one or more than one. The term plurality, as used herein, is defined as two or more than two. The term another, as used herein, is defined as at least a second or more. The terms including and/or having, as used herein, are defined as comprising (i.e., open language).

According to alternative preferred embodiments of the present invention, a device, system, and method, utilize an advanced oxidation process to react with compounds in an environment such as microbes, odor causing chemicals, and other inorganic and organic chemicals. Oxidizers created during advanced oxidation processes are much more effective than traditional oxidants at reacting with compounds such as microbes, odor causing chemicals, and other inorganic and organic chemicals. Oxidants that may be created in an advanced oxidation process are considerably stronger than typical cleaning agents such as chlorine. These oxidants, generally referred to as advanced oxidation product or AOP, include Ozone, Hydroxyl Radicals, Hydro Peroxides, Ozonide Ions, Hydroxides, and Super Oxide ions. All of these compounds are either used during or are produced as a result of advanced oxidation processes. Generally, advanced oxidation product will react with compounds that typically will not react with other common oxidants.

An example of one of the strong oxidizers created by advanced oxidation processes is the Hydroxyl Radical. The Hydroxyl Radical (OH—) is very unstable, thereby making it very aggressive for a free radical. One method that creates the Hydroxyl or free radical is when ozone and water react with ultraviolet light energy and protolysis occurs. Although the Hydroxyl Radicals are very short lived, they have a higher oxidation potential than ozone, chlorine, or hydrogen peroxide, and their unstable nature increases their reaction speed. A strong benefit of advanced oxidation is the end product of carbon dioxide and water.

According to the preferred embodiments of the present invention, by utilizing redundant oxidizers, the speed and efficiency of the oxidation process can be greatly increased, in some cases over 40 times. Oxidants considerably stronger than traditional cleaning chemicals such as chlorine can be created in significant quantities by using a combination of oxidizers in a process as will be discussed below. Oxidants such as Hydroxyl Radicals, Ozone, Hydro Peroxides, and Super Oxide ions can be either used during or are produced as a result of advanced oxidation processes. By utilizing advanced oxidation in a process it creates a reaction in an environment that provides cleansing ions, such as Hydro Peroxide and Super Oxide ions, which react with the surrounding atmosphere and compounds, such as microbes or odor causing chemicals, in an environment. According to a preferred environment of the present invention, an advanced oxidation reaction process occurs when light energy from an ultraviolet light source reacts with oxygen, ozone, a small amount of moisture in air, and a hydrated multi-metallic catalytic surface of a target structure, as will be discussed in more detail below.

An advanced oxidation process, according to a preferred embodiment of the present invention, utilizes a broad spectrum ultraviolet light source that comprises ultraviolet light elements that are targeted onto a multi-metallic catalytic surface of a target structure. This surface preferably comprises a multi-metallic catalytic and hydrophilic material, which may be embodied in many different ways, as will be discussed in more detail below. A hydrophilic surface attracts and absorbs moisture from the surrounding air. Preferably, the broad spectrum ultraviolet light source is used to strike the surface of the target structure as well as to energize the surrounding atmosphere of an environment. The broad spectrum ultraviolet light includes the two bands of ultraviolet light frequencies at about 254 nm wavelength and at about 185 nm wavelength. The ultraviolet energy at 254 nm strikes the target surface and activates production of Hydroxyl Radicals, Super Oxide ions and Hydro Peroxide on the surface. The surface is also preferably hydrophilic thereby absorbing moisture from the surrounding air in the environment. The ultraviolet light energy at 254 nm frequency energizes the catalytic surface causing the surface to react with water molecules in the surrounding air and primarily on the hydrophilic surface causing them to split into Hydroxyl Radicals in an advanced oxidation process, as will be discussed in more details below.

The broad spectrum ultraviolet light source also generates ultraviolet light energy emitted at 185 nm. The photon energy emitted at this wave-length is sufficient to split oxygen molecules to form ozone gas. These ozone molecules in the air are then reduced back to oxygen via a decomposition process initiated by the 254 nm ultraviolet light energy that is also emitted from the broad spectrum ultraviolet light energy source (providing another type of advanced oxidation reaction). The results from this reaction process also produce Hydroxyl Radicals, Super Oxide ions, and Hydro Peroxide similar to the surface reactions discussed earlier. With the photohydroionization process, not only is the target surface active, but also is the air space between the target surface and the ultraviolet light energy source.

Advantageously, this process not only treats the air in the environment with germicidal ultraviolet light energy, but it also has the added effect of continuing to treat the air even after it leaves the surrounding area about the target surface. This process is very effective at reducing microbes, as well as reducing odors and other chemicals in the environment. This is a significant advantage over conventional ultraviolet light and advanced oxidation systems which only reduce microbes and compounds at the point of treatment. The advanced oxidation gas created by the photohydroionization process, according to a preferred embodiment of the present invention, comprises safe and environmentally friendly oxidizers that revert back to oxygen and hydrogen as they react with contaminants. The residual ozone produced as a by-product of the ozone decomposition (advanced oxidation reaction) is a safe low concentration, This advantageous photohydroionization (PHI) process, according to a preferred embodiment of the present invention, creates ozone as well as reduces ozone to safe low levels. This process also requires no maintenance or technician intervention. The process is passive in operation and the surface of the target acts as a catalyst to create the advanced oxidation reactions without actually affecting the target surface itself. This advanced oxidation system and process is far safer than the traditional ozone generators of the past, and much more effective at destroying microbes than conventional germicidal ultraviolet light systems. Additionally, the new and novel advanced oxidation system and process reduces odors in an environment, which germicidal ultraviolet light systems fail to do. The surface of the target being energized by the ultraviolet light along with the surrounding air creates advanced oxidation product while not producing nitric oxide gas or nitric acid, which are recognized irritants and pollutants that are harmful to humans and animals (these are commonly produce by other means of ozone production). The new and novel advanced oxidation process, according to a preferred embodiment of the present invention, produces a combination of powerful oxidizers, such as Hydro Peroxides, Oxide ions, Hydroxyl Radicals, and Super Oxide ions, and further produces redundant oxidation gasses, that can be utilized in a broad range of useful applications.

We need to include mention of the PPC benefit, insulating and containment properties for the UV lamp and mercury. We should also include ways of altering the UV out spectrum via the use of varying voltages and frequencies across the lamp to tune it to our desired output.

Figure 2:
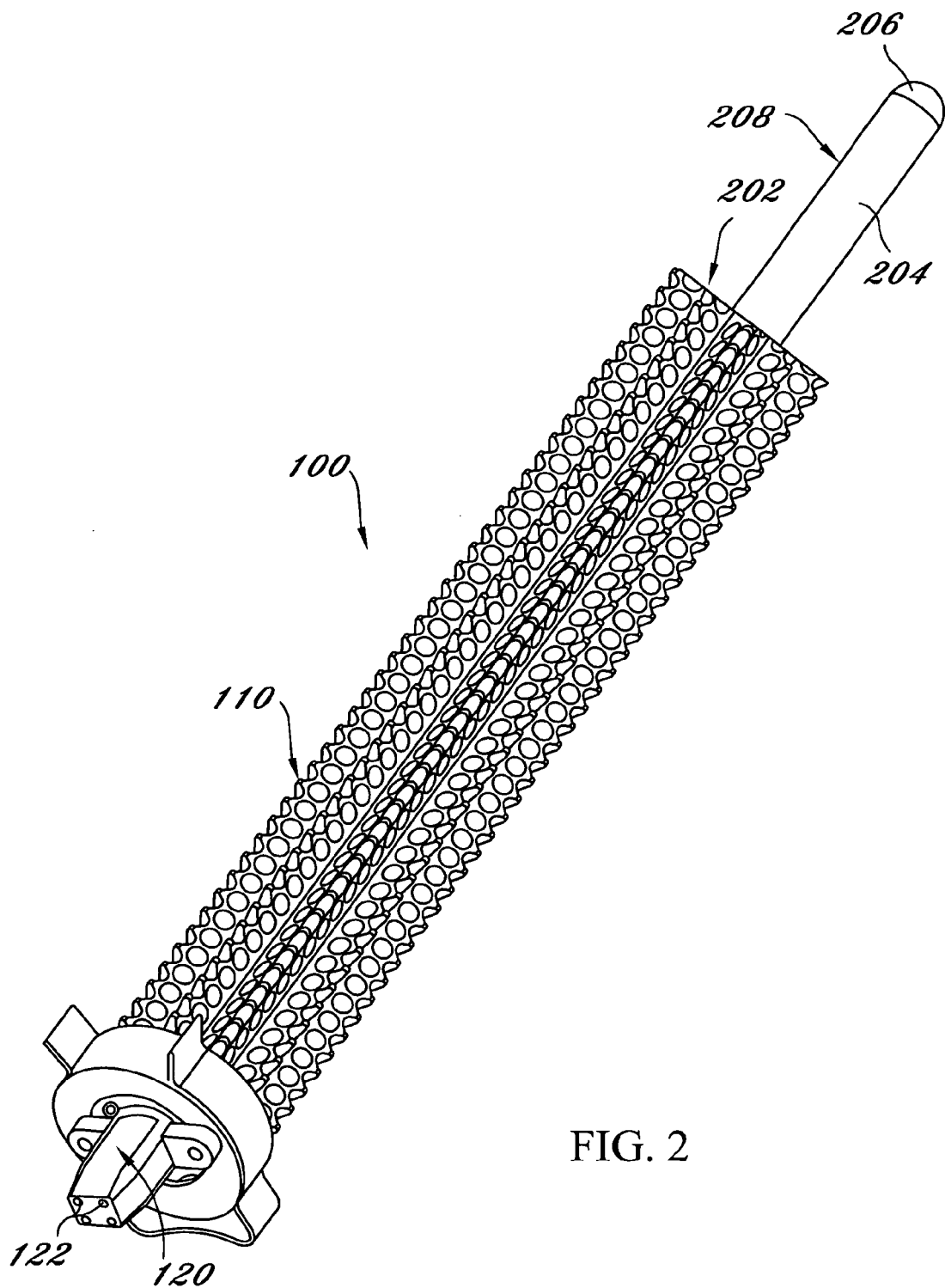
FIG. 2 is a perspective view of the PHI Cell of FIG. 1, having one side partially cut-away to show a portion of an internal UV light source, according to a preferred embodiment of the present invention.

Referring to FIGS. 1 and 2, a photohydroionization (PHI) cell 100 is shown, according a preferred embodiment of the present invention. The PHI cell 100 is an exemplary advanced oxidation reaction unit that can be used in many different applications, as will be discussed below. The PHI cell 100 includes a catalytic target structure 110 that is substantially surrounding an ultraviolet light energy source (not shown in FIG. 1). Preferably, the catalytic target structure 110 is also a hydrophilic structure that absorbs water molecules at the surface of the target structure, as has been discussed above.

The PHI cell 100 includes a base cap 102 and a top cap 104 that in combination structurally support, as an integral unit, the ultraviolet light energy source and the surrounding catalytic target structure 110. Although not shown in FIGS. 1 and 2, according to one exemplary embodiment, a silicon retainer ring (or gasket) and a metal retainer ring in combination inside the base cap 102 operate to secure and seal one end of an ultraviolet light (U.V.) lamp 204 to the base cap 102, and a retainer clip inside the top cap 104 secures the other end of the U.V. lamp 204 to the top cap 104. The base cap 102 and the top cap 104 may also include features or additional structural elements, such as tabs 106, 108, for engaging and further supporting the PHI cell 100 with other structures as should become obvious to those of ordinary skill in the art in view of the present discussion.

At the base cap 102 end of the PHI cell 100, a mating connector end 120 for the ultraviolet light energy source 204, such as a UV lamp 204, is shown with mating connectors 122 for providing electrical contacts for electrically coupling the ultraviolet light energy source 204 to an external electrical power source (not shown). At the base cap 102, in this example, there are mechanical mating structures 130, 132, that mechanically couple the PHI cell 100 to another structure (not shown). For example, the mechanical mating structures 130, 132, can join the PHI cell 100 to a supporting structure (such as a mounting plate) by passing threaded bolts through respective openings at the mechanical coupling structures 130, 132, to secure the PHI Cell 100 to another structure with locking nuts (not shown) that are screwed on to the threaded bolts, e.g., to secure the PHI cell 100 to a mounting plate.

The catalytic target structure 110 preferably includes only a partially closed structure with open areas, such as the holes 112, 114, to allow passage of both the surrounding gasses near the catalytic target surfaces and also to allow passage of a portion of the ultraviolet light energy. In one exemplary embodiment, the mechanical catalytic target structure 110 is approximately 50% active catalytic surface with the remaining area being open area, such as the holes 112, 114, to allow the ultraviolet photon energy to pass out of the target structure 110, thus promoting additional reactions external to the PHI cell 100. According to requirements for different applications, the target structure 110 can vary between 0% (a flow thru cell) and 95% open area, with a preferred open area percentage being between 40% and 60% open area.

The catalytic target structure 110 is preferably shaped to allow for substantially maximum surface area, while limiting the angle of incidence of the ultraviolet photon energy being directed at the target structure 110. For example, a repeating V-shaped geometry in a ridged or pleated design allows for both a correct ratio of open area to closed area as well as maximizing the surface area of the catalytic target 110 that will be exposed for reacting with the ultraviolet light energy and the surrounding environment. As shown in FIGS. 1 and 2, the repeating V-shaped geometry of the surface of catalytic target structure 110 may have a plurality of V-shaped ridges or pleatings. The plurality of V-shaped ridges or pleatings may include apexes formed by panels of catalytic target structure 110 that converge to point away from the ultraviolet light energy source 204 and tips formed by panels of catalytic target structure 110 that converge to point towards the ultraviolet light energy source 204. Further, the plurality of holes 112, 114 may be arranged in rows so that one or more rows of holes 112, 114 extend linearly in a longitudinal direction along the length of each panel forming the apexes and tips of the plurality of V-shaped ridges or pleatings. Also, a plurality of holes 114 may be arranged in rows extending along each of the apexes formed by the panels of the catalytic target structure 110. The longitudinal direction of each of the panels that form the apexes and tips of the plurality of V-shaped ridges or pleatings may be parallel to a longitudinal direction of the ultraviolet light energy source 204. A repeating V-shaped geometry can, of course, be changed or altered to other geometries to accommodate alternative manufacturing requirements, new available manufacturing techniques, textured or faceted surface impingements, rounded or wavy target structures, air or fibrous material, or in general any suitable structure that increases available surface area for the hydrophilic catalytic material to react with the ultraviolet light energy and the surrounding gasses. The PHI cell 100 structure may also be altered from the preferred embodiment to conform to specific structural requirements due to particular applications, as should be obvious to those of ordinary skill in the art in view of the present discussion. For example, large or custom PHI cells may require different structural requirement in particular applications.

Referring to FIG. 2 with continued reference to FIG. 1, the internal ultraviolet light energy source 204 is shown exposed in the cut-away view of FIG. 2 having removed a portion of the catalytic target structure 110 and the top cap 104. The ultraviolet light energy source 204, in this example an ultraviolet light lamp, includes a sealing cap 206 at the top end of the lamp 204. The UV lamp 204 is shown extending outwards at a cut-away end 202 from the catalytic target structure 110. However, in a preferred arrangement the UV light source 204 will be substantially surrounded by the catalytic target structure 110 to substantially maximize the surface area of the catalytic target structure 110 being exposed to the ultraviolet light energy from the U.V. lamp 204. The catalytic target structure 10, in this example, substantially surrounds the ultraviolet light energy source 204 radially along the UV lamp's 204 center axis. This preferably provides for maximum catalytic surface contact for the available U.V. light photon energy. The broad spectrum UV light source 204 is preferably designed to operate in the wavelengths generally ranging between 100 to 300 nm (always including frequency bands about the wavelengths 185 nm and 254 nm). The UV light source 204 can be a low pressure mercury vapor lamp (typically Standard HO or VHO output), medium pressure mercury vapor lamp, or LED based technologies (or any combination of these).

While in this example the catalytic target structure 110 radially surrounds the UV lamp 204, when using LED based technology, LED arrays may be arranged either radially or on a planar axis relative to a catalytic target structure, with the intent of the catalytic target structure being to conform to the overall shape of the LED array to allow for maximum catalytic surface exposure to the UV light source. Other arrangements between at least one U.V. light source and a surface of a catalytic target structure are contemplated by the present discussion, according to design choice of alternative applications, as should become obvious to those of ordinary skill in the art in view of the present discussion. For example, at least one U.V. light source, and preferably a plurality of U.V. light sources, may be located in relatively close proximity to at least one surface of at least one application-specific catalytic target structure in an environment, where the surface of each application-specific catalytic target structure can be particularly shaped and suited for both providing a desired utility in a specific application while also providing a catalytic target surface for enhancing formation of advanced oxidation product at the surface of such application-specific catalytic target structure.

As a more detailed non-limiting example, a plurality of broad spectrum U.V. lamps may be located within an air conditioning duct system, where the internal surfaces of the duct (or ducts) substantially surrounding the plurality of broad spectrum U.V. lamps comprise catalytic target structure material that is substantially in contact with U.V. light photon energy from the U.V. lamps to promote the formation of advanced oxidation product reactions at such surfaces. Of course, each of such U.V. lamps may additionally be radially surrounded by a catalytic target structure 110, as has been discussed above, to additionally promote the formation of advanced oxidation product reactions at the surface of the catalytic target structure 110. As another alternative example that utilizes a plurality of U.V. light sources where at least one of the U.V. light sources is substantially surrounded by a catalytic target structure 110, the outer surfaces of each such catalytic target structure 110 may be exposed to the U.V. light of a U.V. lamp that is outside of, while in proximity to, the particular catalytic target structure 110, thereby additionally promoting the formation of advanced oxidation product reactions at the outer surface of the particular catalytic target structure 110. In general, by contacting with U.V. light photon energy a large amount of the available exposed surface area of at least one catalytic target structure, and according to a particular application a plurality of catalytic target structures, it will accordingly enhance the advanced oxidation product formation process.

The catalytic target structure material is composed of a plurality of compounds particularly at the surface of the catalytic target structure 110. Preferably the catalytic target surface material includes five compounds, i.e., four metallic compounds and a hydrating agent. These compounds preferably include titanium dioxide ($TiO_2$), copper metal (Cu), silver metal (Ag), Rhodium (Rh), and a hydrating agent (such as Silica Gel (tetraalkoxysilanes TMOS, tetramethoxysilane, tetraethoxysilane TEOS)). The hydrating agent may also comprise any suitable compound or combination of compounds that have an affinity to attract or absorb ambient water (i.e., a hydrophilic and hydrating agent). A combination of a plurality of the metallic compounds identified above, and preferably a combination of the four metallic compounds, at the surface of the catalytic target structure 110 comprises a new and novel structure for producing advanced oxidation product reactions for an advanced oxidation process, as will be discussed in more detail below.

Silver has antimicrobial properties. For example, if air strikes the Silver at the surface of the catalytic target 110 it kills microbes in the air. It has been found that Titanium Dioxide combined with Silver at the surface of a catalytic target 110 can multiply by approximately 3 times faster (than using Titanium Dioxide alone without Silver) the formation of the advanced oxidation product reactions, such as formation of the Hydroxyl Radical, Super Oxide ions, and Hydro Peroxides. Copper has antimicrobial properties and also helps speed the reactions at the surface of the catalytic target structure 110 to create the advanced oxidation products. Rhodium has antimicrobial properties and is a catalyst that breaks down Nitrogen compounds and also enhances formation of advanced oxidation products.

The hydrating agent compound significantly increases formation of advanced oxidation product reactions (primarily Hydroxyl Radical production, on the surface of the catalytic target structure 110 and within the environment surrounding the catalytic target 110). Ambient humidity as well as induced humidity (via either forced evaporation, ultra-sonic atomizing, or other suitable means) in the environment surrounding the catalytic target 110 will typically provide humidity at the surface of the catalytic target 110 thereby providing a hydrating agent (i.e., the water) at the surface of the catalytic target 110 to promote the formation of advanced oxidation product reactions. Additionally, ambient humidity as well as induced humidity can be drawn to the catalytic target surface by a hydrophilic and hydrating agent compound, such as the Silica Gel, at the surface of the catalytic target 110 to significantly enhance the formation of advanced oxidation product reactions at the surface of the catalytic target 110. This is an especially significant advantage of the present invention.

Combinations of the above discussed five compounds can vary between less than 1 percent to greater than 90 percent of any one of these five compounds, as may be desired for different applications according to alternative embodiments of the present invention. Different manufacturing techniques and methods may be used to provide the surface of the catalytic target structure 110 with a combination of the desired compounds discussed above. For example, a coat including the desired compounds can be provided to the surface of the catalytic target structure 110. These different manufacturing techniques and methods can include but are not limited to adhesives, polymers, baking (low and high heat applications), electrical charging, and pigment carrier technology. In addition, other non-specified compounds may be added to the combination of five compounds in order to facilitate adhesion and/or bonding to any particular surface of a catalytic target structure 110, as should be obvious to those of ordinary skill in the art in view of the present discussion.

According to one non-limiting example, a combination of the preferred five compounds can be provided in a mixture that also includes a base solvent to provide a mixture solution. The mixture solution can then be deposited, such as by spraying or by other known deposition method, on to the surface of the catalytic target structure 110. The base solvent will then evaporate leaving the desired combination of compounds at the surface of the catalytic target structure 110. The method used for providing a combination of the desired compounds to a surface of a catalytic target structure 110 will be entirely dependant on the design choice for commercially available technology for making the specific target structure to be used in an application.

Figure 3:
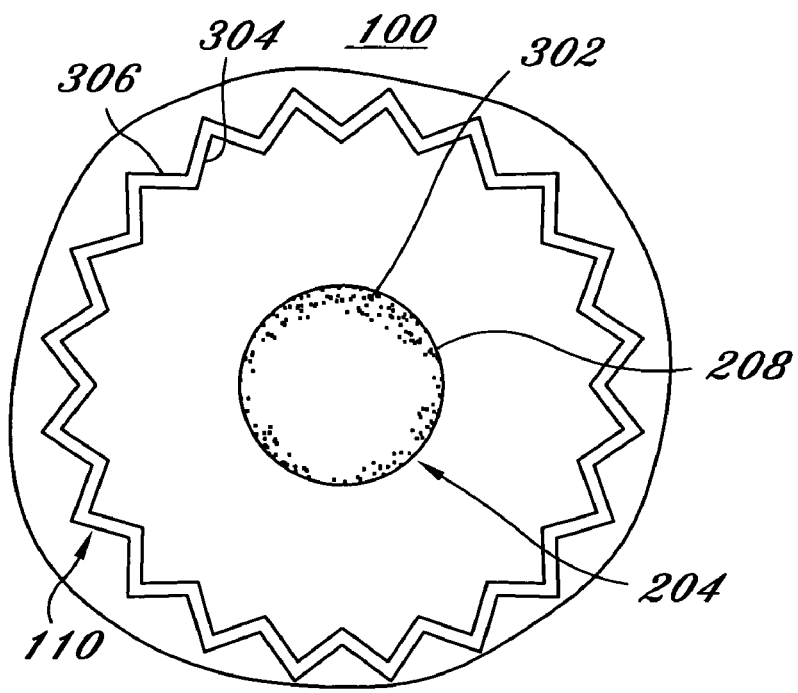
FIG. 3 is a diagram representation of a cross-sectional side view of the PHI Cell of FIG. 1, illustrating the internal UV light source and a surrounding catalytic target structure, according to a preferred embodiment of the present invention.

Referring to FIG. 3, a diagram representation of a cross-sectional side view of the exemplary PHI cell 100 is shown, according to a preferred embodiment of the present invention. The internal UV lamp 204 is substantially surrounded by the external catalytic target structure 110. The UV lamp 204, in this example, contains mercury vapor gasses 302 that when energized (such as by electric energy provided via the electrical contacts of the mating connectors 122) at the appropriate frequencies will create a broad spectrum ultraviolet light energy that is radiated from the UV lamp 204. The UV lamp 204 has an outer surface that preferably is substantially coated with a protective barrier coating, in this example, with a fluorocarbon protective coating or film 208 that substantially encases the UV light source 204 and is manufactured of a material, such as preferably fluorocarbon or other protective plastic coating or barrier material, that allows the UV light to substantially pass through the protective barrier coating. One primary purpose of this external protective barrier coating or film structure 208 is to provide an insulated barrier to the UV light source, thereby preventing heat loss in cool operating environments, reducing temperature shock, and thus optimizing the UV light source efficiency. This external protective coating structure 208 also acts as a physical barrier (a containment barrier) preventing either quartz, glass, mercury or other materials used in the construction of the UV light source 204 from leaving the fluorocarbon protective barrier coating 208, i.e. in case of accidental breakage or damage to the PHI cell 100. Another significant benefit to this fluorocarbon coating or film structure 208 is that it deters debris and other contaminants from contacting and possibly adhering to the UV light source 204 and potentially reducing it's operating efficiency or more importantly physically damaging it. Preferably, the protective barrier coating 208 is made of fluorocarbon material that provides an external non-polar surface that does not attract external contaminants or pollutants thereby providing an anti-fouling protective barrier surface for the UV light source 204. This new and novel structure and arrangement allows all of the U.V. light energy from the UV light source 204 to be emitted out of the protective barrier coating 208. The protective coating structure 208, in this example, can be a shrink tube type film or coating structure at the outer surface of the UV lamp 204. However, other protective and/or coating structures may be used either at the inner surface and/or at the outer surface of the U.V. lamp 204, as should be obvious to those of ordinary skill in the art in view of the present discussion. Additionally, the material, shape, and texture, of the coating structure can be varied to alternative materials, shapes, and textures, from the present example of a fluorocarbon shrink tube, as long as an alternative coating material, shape, and texture, allows the U.V. light to pass through the alternative coating structure such that the U.V. light photon energy can contact the surface of the catalytic target structure 110 to promote the advanced oxidation product formation reactions at the surface of the catalytic target structure 110.

The catalytic target structure 110 includes an inner surface 304 and an outer surface 306. The inner surface 304 is directly exposed to the internal UV lamp 204. The inner surface 304 receives ultraviolet light energy directly from the UV lamp 204. The external surface 306 is preferably also coated with the catalytic material such that it can be exposed to ultraviolet light energy from either an external ultraviolet light source or possibly reflected ultraviolet light from the internal UV lamp 204, i.e., U.V. light reflecting from an external reflective surface (not shown). Specifically, this reflected UV light may originate at the UV lamp 204, then pass through openings 112, 114, of the catalytic target structure 110 (see FIG. 1), and then reflect from an external structure back to the outer surface 306. In this way the catalytic target structure 110 substantially maximizes the exposed surface area to substantially maximize the advanced oxidation product formation reactions at the surfaces 304, 306, and in the surrounding gas environment.

Figure 4:
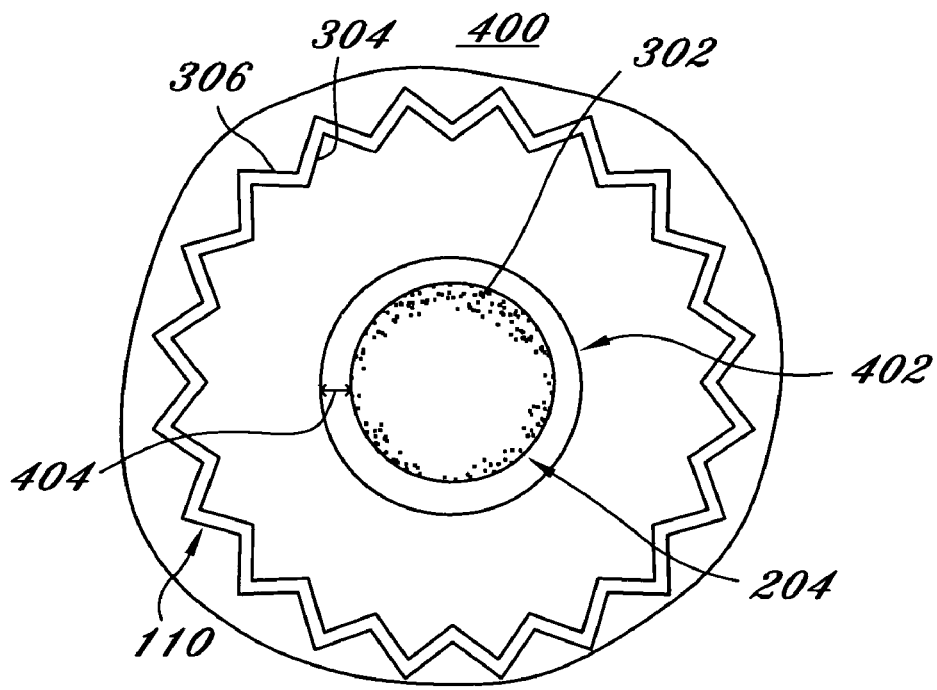
FIG. 4 is a diagram representation of a cross-sectional side view of an alternative PHI Cell, illustrating the internal UV light source and a surrounding catalytic target structure, according to an alternative preferred embodiment of the present invention.
Figure 5:
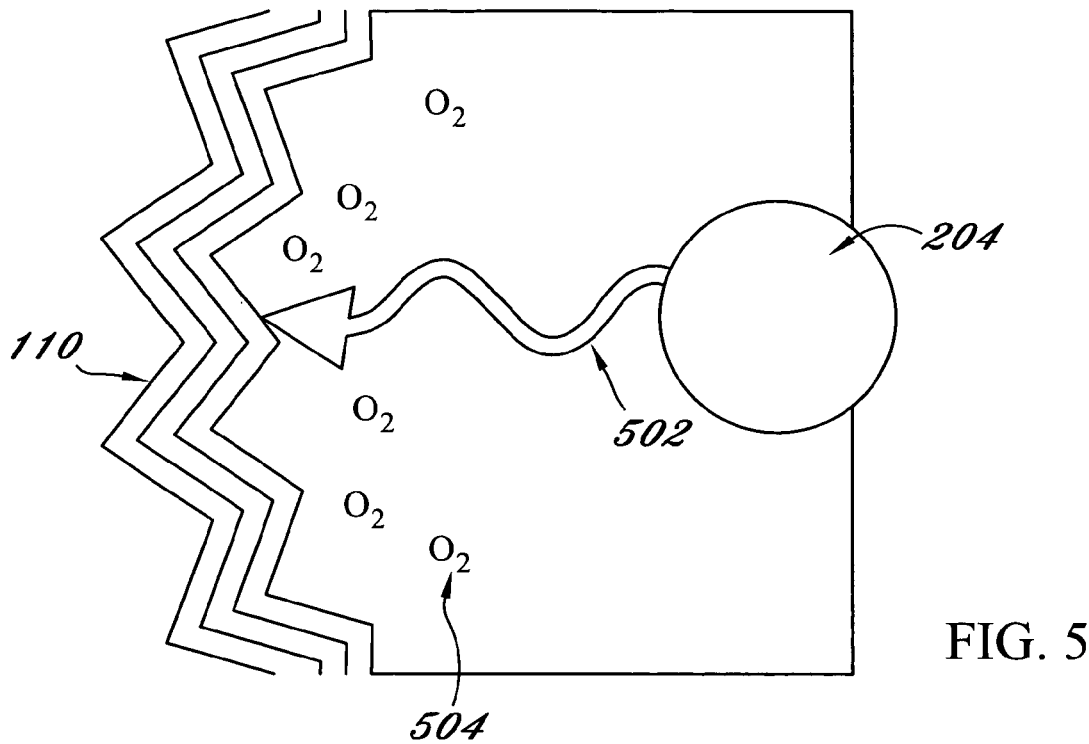
FIGS. 5 to 8 are diagram representations of cross-sectional side views of a portion of an exemplary PHI Cell, showing an advanced oxidation process to create advanced oxidation product on the surface of a catalytic target structure and in the surrounding environment, according to one embodiment of the present invention.

Referring to FIG. 4, an alternative arrangement for a PHI cell 400 is shown, according to a preferred embodiment of the present invention. This alternative PHI cell 400 includes a variation on the internal UV light source such that the UV lamp 204 is surrounded by a barrier structure 402 that is sufficiently transparent to the U.V. light emitted from the U.V. lamp 204 to allow the U.V. light to pass through the barrier structure 402 and contact the surface 304 to promote the formation of advanced oxidation product reactions at the surface 304. Preferably, the barrier structure 402 is located within close proximity 404 from the outer surface of the UV lamp 204. In this alternative embodiment, the surrounding barrier structure 402 comprises a clear tube of material, such as quartz, that is sufficiently transparent to the ultraviolet light energy about the frequencies of interest, i.e. about 100 to 300 nm wavelengths. This external barrier structure 402 substantially surrounds and encases the internal UV lamp 204 for the entire length of the UV lamp 204. The outer barrier tube 402 and the surface of the inner UV lamp 204, in this example, are in close proximity 404 (at a nominal distance), and preferably a silicon or Teflon seal creates a bonding seal between the ends of the barrier tube 402 and the ends of the inner UV lamp 204. This outer tube 402 provides a containment barrier in the event that the inner UV lamp 204 is broken (e.g., to contain the mercury vapor 302 and any broken glass and debris due to the broken U.V. lamp 204), and also provides the benefit of thermal protection of the UV lamp 204 thereby significantly extending the usable life of the ultraviolet light energy source 204 and maximizing output efficiency by thermally stabilizing the light energy source 204, as well as protecting the light energy source 204 from wet environments (condensation in cold environments, etc).

In general, the design and arrangement of a catalytic target preferably takes into account 1) the distance from the UV light source, and 2) how to maximize the exposed surface area of the catalytic target, for enhancing the formation of advanced oxidation product. The closer the catalytic target is to the UV light source, the higher the UV light photon energy that will be provided to the surface area of the catalytic target. Additionally, the exposed surface area of the target should be maximized to allow maximum surface area to contact with U.V. light photon energy and with the surrounding environment for maximizing the reactions to form and activate the advanced oxidation products. Preferably the catalytic target comprises a ridged or pleated design to maximize the surface area exposed to the UV light photon energy and to the surrounding environment.

Figure 6:
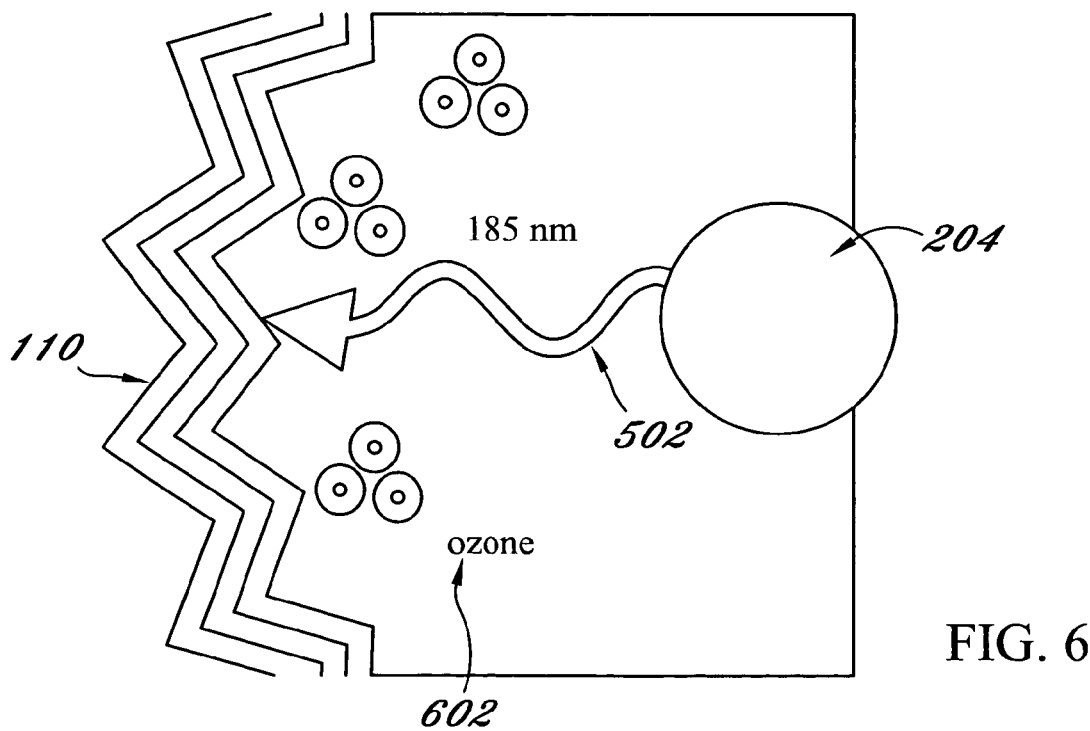
Figure 7:
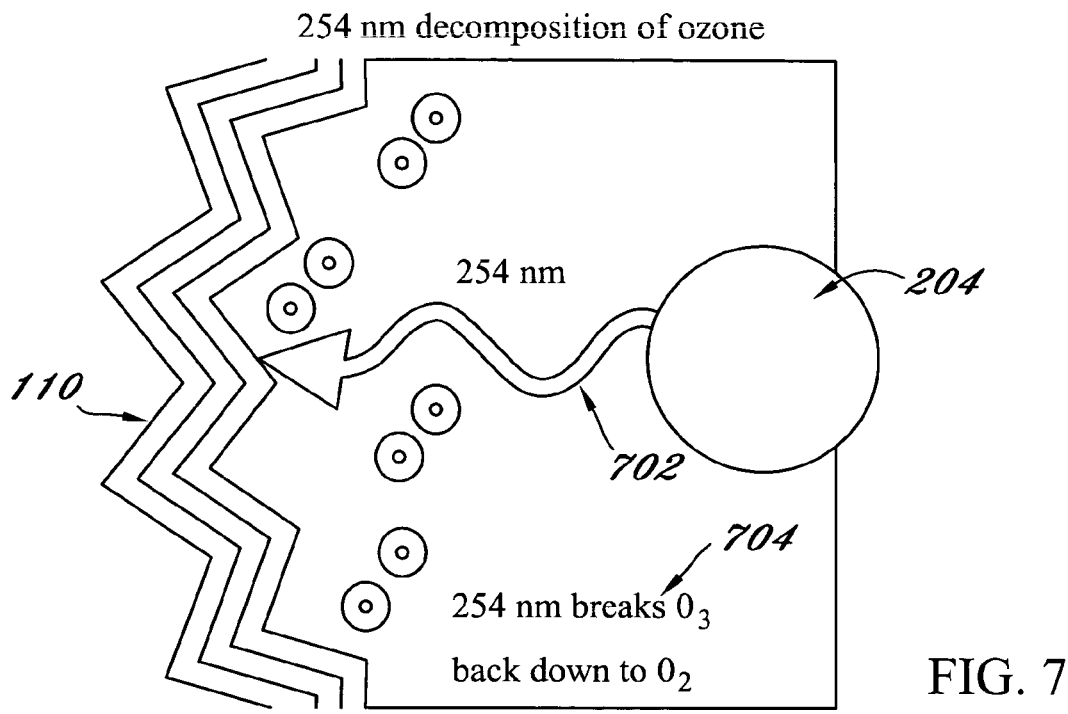

With reference to FIGS. 5, 6, 7, and 8, the formation of advanced oxidation product process will be discussed in more detail below. According to an exemplary embodiment of the present invention, ultraviolet light energy from a U.V. light source 204 is emitted and directed to the surface area of a catalytic target structure 110, as has been discussed above and as shown in FIG. 5. The ultraviolet light energy includes frequencies at about 185 nm wavelength 502 which interact with oxygen 504 in the environment to create ozone 602, as illustrated in FIG. 6. Ozone is a strong oxidizer that can kill microbes, such as bacteria, mold, viruses, and can also react with chemicals in the environment to reduce odors. The UV light source 204 contemporaneously with emitting the 185 nm UV light energy also emits UV light energy at about 254 nm wavelength 702, as illustrated in FIG. 7. This UV light energy at 254 nm breaks down 704 the ozone back to oxygen and thereby also advantageously releasing Hydroxyl Radicals and other advanced oxidation products. Additionally, the U.V. light energy at 254 nm 702 contacts the surface of the catalytic target structure 110. The catalytic target structure 110 includes the hydrating agent which, preferably also comprising a hydrophilic agent, has attracted moisture from the air in the surrounding environment to the surface of the catalytic target structure 110. The U.V. light energy at 254 nm 702 contacting the surface of the catalytic target structure 110 reacts with the water molecules and the collection of metals at the surface to create advanced oxidation products such as Hydroxyl Radicals, Hydro Peroxides, Super Oxide Ions, that are highly reactive and will react with the surrounding environment to kill microbes, reduce odors, and will react with and destroy other undesirable organic and inorganic chemicals found in the environment. This results in a cleaning and purifying treatment of the surrounding air of an environment. These advanced oxidation products are very short lived and highly reactive such that after reacting with the compounds in an environment the advanced oxidation products will (over a short period of time) revert to safe and harmless oxygen and water molecules. Further, ozone created in the process will quickly break down and revert back to oxygen 704 such that ozone levels in the environment will normally remain at safe low levels immediately after the advanced oxidation process has cleaned the environment of microbes, odors, and other undesired compounds and impurities. Additionally, the U.V. light energy at 254 nm wavelengths exhibits germicidal properties and beneficially kills germs and microbes that are in direct contact with the UV light energy. This also helps to kill microbes in the surrounding air and in an environment. Additional wavelengths are also utilized from 100-300 nm to react with compounds with activation energies corresponding to the different wavelengths of the UV light source 204.

Figure 8:
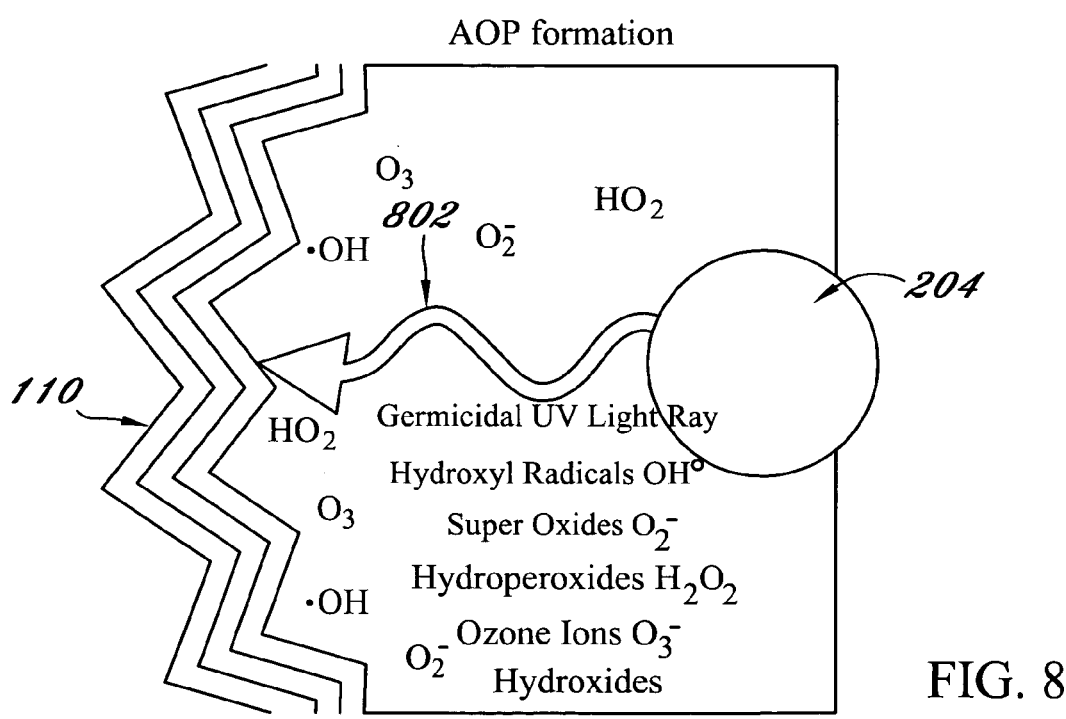

FIG. 8 illustrates an overall exemplary advanced oxidation product formation process, according to a preferred embodiment of the present invention. A broad spectrum U.V. light energy 802 from the U.V. light source 204 interacts with the surrounding environment as well as contacts the surface of the catalytic target structure 110. In this instance the 185 nm wavelengths from the broad spectrum U.V. light source 204 substantially creates ozone and at substantially the same time at the 254 nm wavelengths destroys ozone and converts it back to oxygen. A combination of the ozone creation and destruction in the atmosphere of the environment about the U.V. light source 204 and the reaction at the surface of the hydrated catalytic target structure 110 creates the multiple benefits of germicidal U.V. light rays, Hydroxyl Radicals, Super Oxide Ions, Hydro Peroxides, Oxide Ions, and Hydroxides, and other such advanced oxidation products. The surface combination of advanced oxidation products and germicidal U.V. light rays contemporaneously provide the benefit of significant microbial reductions, reduced odors, and removal of certain undesirable chemicals in the environment. For example, the advanced oxidation process destroys the following: paint, pet odors, sewer odors, volatile organic compounds, chemical fumes, cleaning chemical odors, cooking odors, decaying organic matter, viruses, fire and smoke, garbage odors, hydrocarbons, mold and mildew, and other microorganisms.

Figure 9:
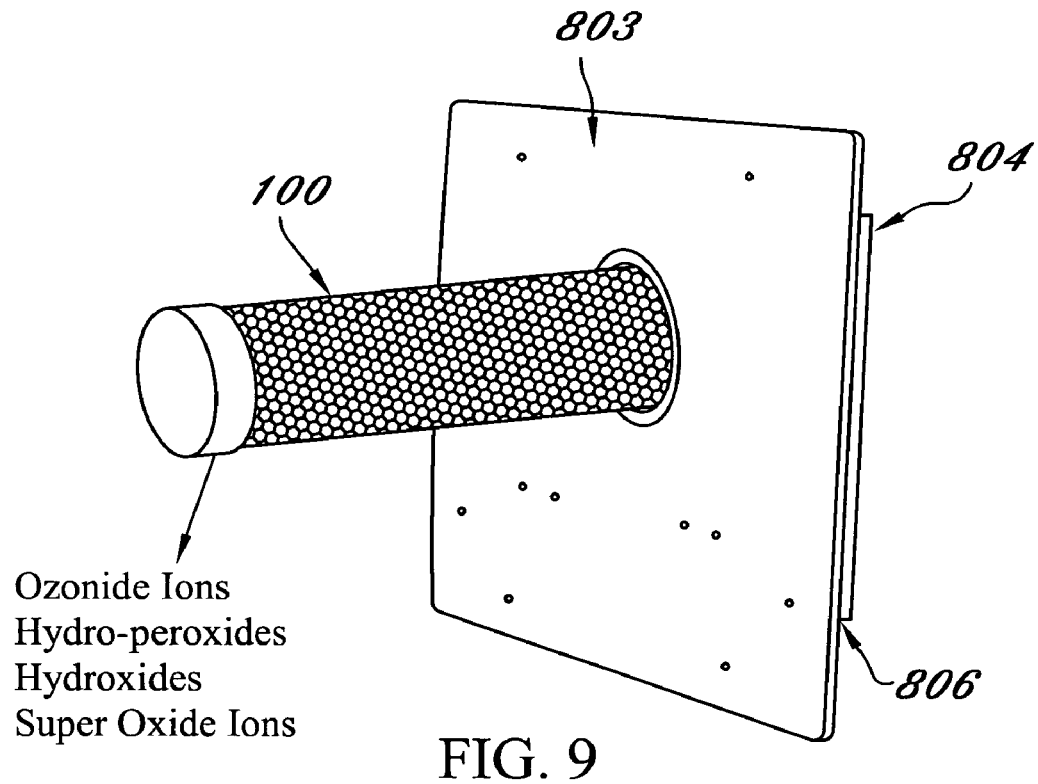
FIG. 9 is a perspective view of an exemplary application of a PHI cell on a mounting plate, in accordance with one preferred embodiment of the present invention.
Figure 10:
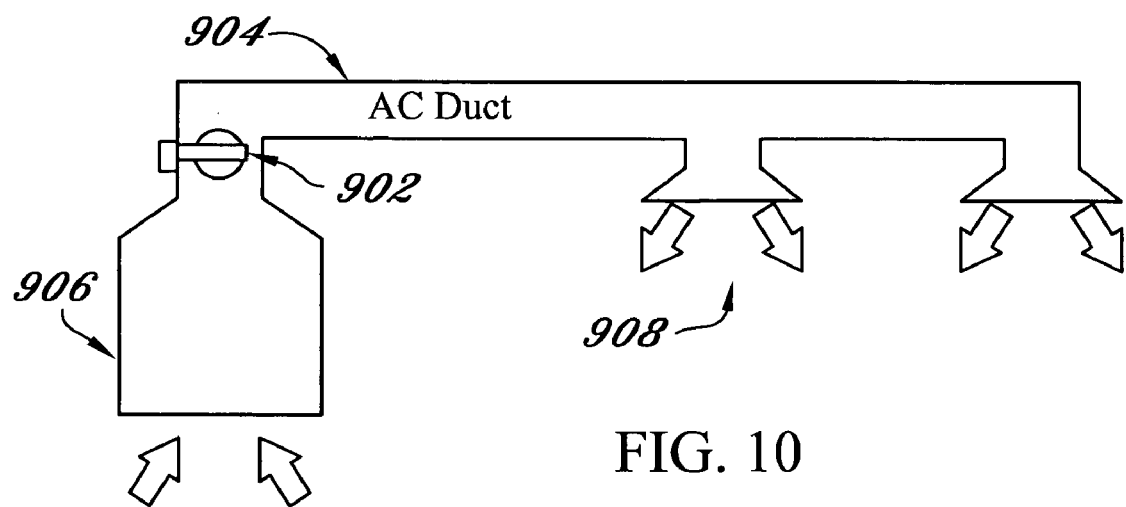
FIG. 10 is a diagram representation of a cross-sectional side view of an exemplary air condition (AC) duct system including a PHI Cell mounted in the AC duct system, according to a preferred embodiment of the present invention.
Figure 11:
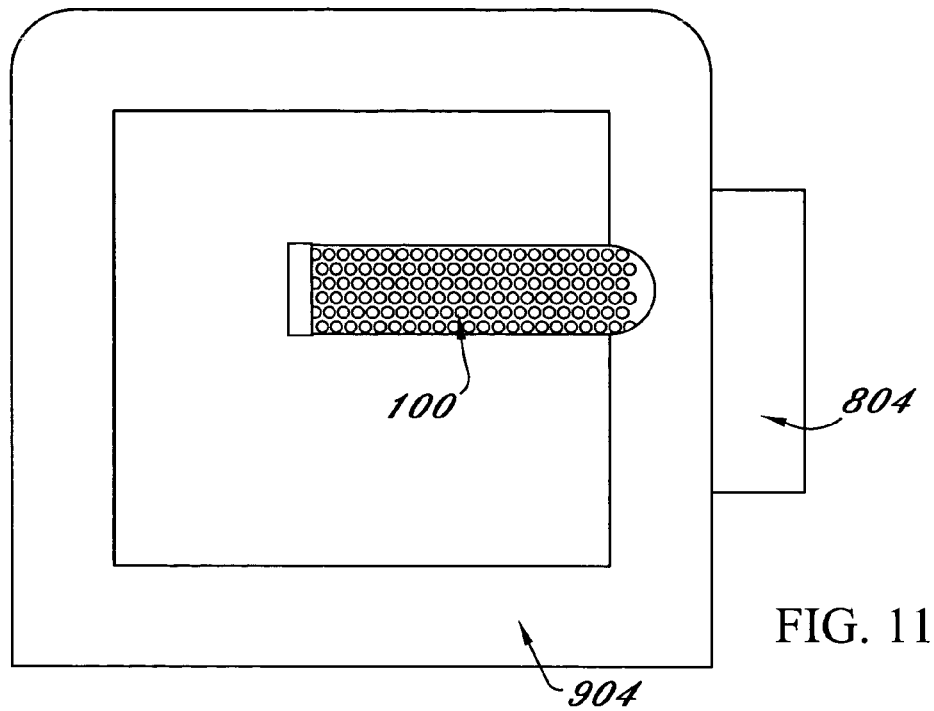
FIG. 11 is a bottom view of an AC air return duct showing a PHI Cell mounted in the AC duct system, according to one preferred embodiment of the present invention. We need to include other embodiments, stand alone units with internal air movers (fans), stand alone units utilizing convection.

Referring to FIGS. 9, 10, and 11, an exemplary application of the new and novel advanced oxidation process is illustrated, in accordance with one of the preferred embodiments of the present invention. A system for purifying and cleaning an air conditioning and/or heating (AC) duct system is shown utilizing the new and novel advanced oxidation process to eliminate sick building syndrome risks by, for example, reducing odors, air pollutants, chemical odors, smoke, mold, bacteria, and viruses. As shown in FIG. 9, a PHI cell 100 is mounted at it's base cap 102 onto a mounting plate 803 that provides structural support for the PHI cell 100 when located inside an AC duct 904 (see FIG. 10). On the opposite side of the mounting plate 803 is shown an enclosure 804 that contains electronic circuits for powering and controlling the PHI cell 100. The enclosure 804, for example, includes a power supply and a ballast circuit for energizing the PHI cell 100. Additionally, according to an alternative embodiment of the present invention, a fiber optic cable 806 extends from the PHI cell 100 through the mounting plate 803 and the enclosure 804 to provide a light indicator that indicates when the PHI cell 100 is in use. This fiber optic light indicator 806 can be used by a monitoring system, for example, to detect failure conditions such as when the PHI cell 100 is not properly functioning and may need to have a U.V. lamp 204 replaced. Additionally, the fiber optic light indicator 806 can provide the means to monitor and control the operation of the PHI cell 100 under various applications. One end of the fiber optic cable 806 is preferably in substantial contact with the broad spectrum ultraviolet light that is being emitted from the U.V. light source 204 in the PHI cell 100 while the other end of the fiber optic cable 806 preferably emits visible light as an indication that the U.V. light source 204 in the PHI cell 100 is operational. The fiber optic cable material can provide a filtering effect for the U.V. light being transmitted through the fiber optic cable such that the emitted light out of the fiber optic cable indicator 806 is mostly in the visible light range and safe to use by most equipment and applications. Optionally, a filter (not shown) may be inserted at any point between the U.V. light from the PHI cell 100 and the output of the fiber optic cable indicator 806 such that the filter will substantially remove undesired U.V. light energies (e.g., at undesired frequencies) while permitting light in the visible range to be emitted from the fiber optic cable indicator 806. In summary, the fiber optic cable 806 (any suitable type may be used) provides a means to monitor the PHI cell 100 status. As a safety feature either the cable itself, or a secondary filter, is used to absorb the 100 to 300 nm wavelengths, while allowing the visible light portion (typically in the 500 nm range) to be transmitted out from the fiber optic cable to be used, for example, at a remote display point which then can directly indicate PHI cell 100 status. Alternatively, the fiber optic cable material may also be made of any suitable material that will transport the UV light (100-300 nm) to a photo detector (not shown) so as to enable a real-time method of monitoring and optionally controlling the U.V. lamp's 204 output. Also, this photo detector and sensor can be coupled to a variable frequency, variable voltage, power supply (not shown) for power the U.V. lamp 204 such that it can then be used to regulate and change the overall U.V. lamp output power (photon energy) and the frequency specific output energy at one or more ranges of U.V. light frequencies. This is a valuable feature of preferred embodiments of the present invention.

For example, with reference to FIG. 12, an exemplary functional block diagram of a system 1200 utilizing the new and novel PHI Cell 100 will be discussed below. The system 1200 includes at least one PHI Cell 1202 including a fiber optic cable 1204 that delivers at its output, for example, a light signal indicating the U.V. light operational status of a respective PHI Cell 1202.

According to a preferred embodiment of the present invention, visible light emitted from the fiber optic cable 1204 would act as a direct mechanical indicator of the at least one PHI cell's 1202 operating status. A fiber optic element coupled directly to the UV source 204 in a PHI cell 100 (see FIG. 1), would be preferably equipped with UV filtering properties, or alternatively with the addition of a separate UV filter (not shown), that can be used to transmit the visible light emitted from the PHI Cell 1202 (typically in the 400 to mid 500 nm range) to a remote location or unit panel to monitor PHI cell status. Examples of these two installation types would be: a display panel on a piece of equipment, or for remote installations (such as would be needed in some HVAC system installations) an indicator positioned remotely from the PHI unit. The light transmitted down the fiber optic cable 1204 would be terminated at a lens (not shown) that would illuminate and act as a visual display (not shown) for an operator to monitor or other equipment to monitor.

For example, a photo detector or photo meter (not shown) coupled to a computer system 1208 could be used to automatically monitor the ON/OFF status of the at least one PHI Cell 1202. The computer system 1208, in the event of detection of a fail condition, such as when the at least one PHI Cell 1202 should be ON but it is detected as being OFF (e.g., no UV light detected or not detected above a predetermined power level) at the photo detector or photo meter, can then send an alert signal to a user and/or operator and/or technical personnel (which may also be referred to herein as user/operator/technical personnel). The alert signal can include an audible signal (such as by an audible alarm sound), a visual signal (such as by a light on a console display or by a light source at a location readily visible by a user/operator/technical personnel, and can even include a data signal, such as an email message, sent to a remote computer (not shown), or even a wirelessly transmitted signal sent to a persons' portable unit (not shown), such a cellular telephone or paging device, that can then alert the user/operator/technical personnel of the monitored fail condition even if the user/operator/technical personnel is remotely located from the particular installation of the at least one PHI Cell 1202 at a facility. Alternative monitoring system configurations and operations should be obvious to those of ordinary skill in the art in view of the present discussion.

Figure 12:
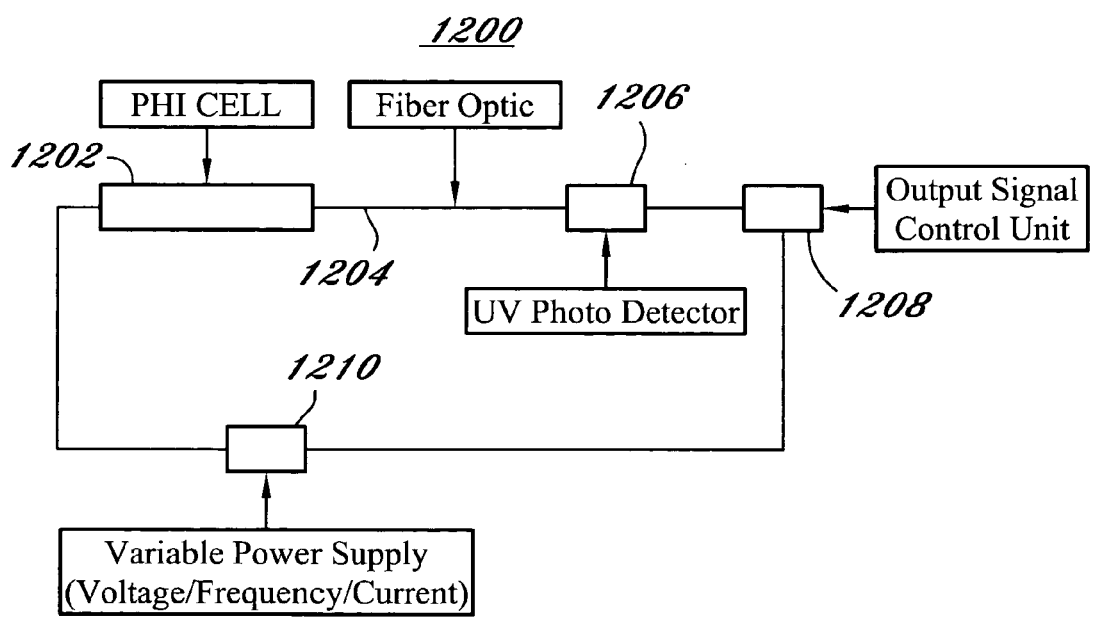
FIG. 12 is an exemplary functional block diagram of a system utilizing the new and novel PHI Cell, according to an embodiment of the present invention.

Continuing with reference to FIG. 12, according to another preferred embodiment of the present invention, the system 1200 may use in the fiber optic cable 1204 UV transparent fiber optic material (such as quartz) as a means for transmitting the actual UV light waves that are generated by the UV lamp 204 (see FIG. 1). The fiber optic cable 1204, thus equipped with the UV transparent fiber optic material (such as quartz), is preferably directly mechanically coupled to the UV lamp 204 (no air spaces) to collect the entire 100-300 nm range of UV light being emitted by the UV source 204, and thereby to transmit the UV light (via optical coupling) from the at least one PHI Cell 1202 to a UV photo detector 1206 that would then analyze the UV light spectrum emitted from the UV lamp 204 for each of the at least one PHI Cell 1202. The UV photo detector 1206, according to this alternative embodiment, comprises a photo meter or other optical spectrum analyzing equipment that provides an output via a user interface such as via a display (not shown) to a user/operator/technical personnel. This would enable the user/operator/technical personnel to directly monitor and quantify the actual UV wavelength and energy output of the at least one PHI cell 1202. This can be done local to the installation of the at least one PHI Cell 1202 or can be done remotely, such as by delivering the UV light signal via the fiber optic cable 1204 to a remotely located UV Photo Detector 1206.

According to another alternative embodiment of the present invention, the same method as discussed above may be used, with the addition of a computer control system 1208 coupled with the UV Photo Detector 1206. The UV photo detector 1206, according to this alternative embodiment, comprises a photo meter or other optical spectrum analyzing equipment that provides an output data signal indicative of an operational status of the at least one PHI Cell 1202. A controller 1208 can monitor a data signal from the UV Photo Detector 1206 to determine a fail condition, such as an OFF status detected for any of the at least one PHI Cell 1202, or such as an out of normal operational tolerances condition for any of the at least one PHI Cell 1202. The data signal collected from the UV Photo Detector 1206 could then be used to adjust an adjustable power supply 1210 that is providing power to the at least one PHI Cell 1202. The computer control system 1208 can provide an output signal to a user interface to provide information to a user/operator/technical personnel who can then instruct the computer control system 1208 how to adjust the power output of the at least one PHI Cell 1202. Optionally, the computer control system 1208 can automatically adjust the power output of the at least one PHI Cell 1202. Additionally, the computer system 1208 can monitor the condition of the at least one PHI Cell 1202, and then can send an information/alert signal to a user and/or operator and/or technical personnel (which may also be referred to herein as user/operator/technical personnel). The information/alert signal can include an audible signal (such as by an audible sound), a visual signal (such as by at least one light on a display or by at least one light source at a location readily visible by a user/operator/technical personnel, and can even include a data signal, such as an email message, sent to a remote computer (not shown). The information/alert signal can even include a wirelessly transmitted signal sent to a persons' portable unit (not shown), such a cellular telephone or paging device, that can then inform/alert the user/operator/ technical personnel of the monitored condition even if the user/operator/technical personnel is remotely located from the particular installation of the at least one PHI Cell 1202 at a facility. Alternative monitoring system configurations and operations should be obvious to those of ordinary skill in the art in view of the present discussion.

The adjustable power supply 1210 can be adjusted to vary at least one of the frequency, the current, and the voltage, of an output power signal being coupled to each of the at least one PHI Cell 1202. By adjusting the adjustable power supply 1210 it varies the output electrical power signal, such as its voltage level or its AC frequency, that then is delivered to the at least one PHI Cell 1202. This would enable a user/operator/ technical personnel, or the automated controller 1208, or both, to control the operation of the at least one PHI Cell 1202. A user/operator/technical personnel, or the automated controller 1208, for example, could "dial in" (adjust) the adjustable electrical power signal for adjusting the U.V. source output for the at least one PHI cell 1202, such as the total output power or the output power levels at one or more frequency ranges such as to meet a particular output energy profile, according to a requirement for a specific application or to ensure the optimum output of the at least one PHI ell 1202 is achieved over its working life.

Referring again to FIGS. 9, 10, and 11, an exemplary system and application of the new and novel PHI Cell 100 are shown, and will be discussed below. As illustrated in FIGS. 9 and 10, the PHI cell 100 and mounting plate 803 are arranged and mounted onto an AC duct 904 in a mounting arrangement 902 such that the air flow through the AC duct 904 passes and contacts the PHI cell 100. As shown in FIG. 10, the PHI cell 100 extends substantially within the AC duct 904 through an opening in one of the walls of the AC duct 904 and is supported in place by a mounting plate 803 (shown in FIG. 9) and an external enclosure 804 that contains the circuits powering and controlling the PHI cell 100. The enclosure 804 may also be mounted remotely to allow installation in areas were adequate space is not available.

The air intake 906 receives air from the building environment, which includes pollutants, odors, mold, bacteria, virus, and other undesired chemicals. As this air passes through the duct 904 it comes in contact with as well as exposed to the PHI cell 100 and the U.V. light and the advanced oxidation processes, as has been discussed earlier, will substantially clean and purify the air. This air is then driven through the remaining AC duct 904 in combination with the advanced oxidation products created in the PHI cell, where as the remaining advanced oxidation products created in the PHI cell continue to reduce the residual pollutants as they travel down the duct with the air. Any remaining advanced oxidation products then exit into the room where they continue to quickly reduce any additional ambient pollutants encountered. Additionally, germicidal UV light rays help destroy microorganisms, such as germs, molds, viruses, and bacteria passing through the A.C. duct 904. In this way, the advanced oxidation process, in combination with the germicidal U.V. light rays, provided by the PHI cell 100 in this application, thereby cleans and purifies air for use in a building environment.

According to another alternative embodiment of the present invention, the PHI cell 100 is intended to be used as a modular system that can either be used singularly or in plurality (limited only by the specific application). The PHI cell 100 itself may be adapted to conform to multiple types of installations. In one embodiment the PHI cell 100 is mounted via an attached plate to facilitate treatment in many different types of installations, such as in an HVAC system (e.g., in an AC duct system as has been discussed above). In yet another embodiment the PHI cell 100 is attached via flexible clips to a rigid structure (sometimes with a fan assembly) to facilitate treatment of air in a multitude of applications.

The advanced oxidation processes, as provided by alternative embodiments of the present invention in view of the discussion above, consist of reactions with any combination of Hydroxyl Radicals, Super Oxide Ions, Hydro Peroxides, Ozonide Ions, and Hydroxides, and other such advanced oxidation products, that revert back to oxygen and hydrogen after the oxidation of the pollutants. Additionally, in certain alternative embodiments, germicidal UV light rays can additionally help destroy microorganisms, such as germs, molds, viruses, and bacteria. In this way, the advanced oxidation processes, and optionally in combination with the germicidal U.V. light rays, clean and purify an environment by reducing microorganisms, odors, and other undesirable chemicals in the environment. The advanced oxidation processes, as provided by the alternative embodiments of the present invention, can be very useful in many different applications, as should be obvious to those of ordinary skill in the art in view of the discussion above.

While there has been illustrated and described what are presently considered to be the preferred embodiments of the present invention, it will be understood by those of ordinary skill in the art that various other modifications may be made, and equivalents may be substituted, without departing from the true scope of the present invention. Additionally, many modifications may be made to adapt a particular situation to the teachings of the present invention without departing from the central inventive concept described herein. Furthermore, an embodiment of the present invention may not include all of the features described above. Therefore, it is intended that the present invention not be limited to the particular embodiments disclosed, but that the invention include all embodiments falling within the scope of the appended claims.

What is claimed is:

1. A photohydroionization cell comprising:
    an ultraviolet light source for providing broad spectrum ultraviolet light in the 100 nm to 300 nm range; and
    a one-piece catalytic target structure mechanically coupled to and substantially surrounding the ultraviolet light source, the catalytic target structure including:
        a surface that, after contact with ultraviolet light, reacts with hydrate at the surface to form advanced oxidation product, the surface having a repeating V-shaped geometry comprising a plurality of V-shaped pleatings that generally surround a circumference of the ultraviolet light source, the plurality of V-shaped pleatings including: (i) apexes formed by panels of the catalytic target structure that converge to point away from the ultraviolet light source and (ii) tips formed by panels of the catalytic target structure that converge and point towards the ultraviolet light energy source; and
        a plurality of holes configured to allow passage of both surrounding gases and a portion of the ultraviolet light through the target structure, wherein the holes are arranged in rows that extend linearly in a longitudinal direction along the length of the panels that form the apexes and the tips of the plurality of V-shaped pleatings.

2. The cell of claim 1, wherein the holes are circular.

3. The photohydroionization cell of claim 1, wherein the surface of the catalytic target structure comprises a top portion and a bottom portion for contact with the ultraviolet light provided by the ultraviolet light source for reacting with hydrate at such surface to form advanced oxidation product.

4. The photohydroionization cell of claim 3, wherein the surface of the catalytic target structure is designed for substantially maximum catalytic surface contact with the ultraviolet light provided by the ultraviolet light source.

5. The photohydroionization cell of claim 1, wherein the surface of the catalytic target structure is designed for contact with ultraviolet light provided by the ultraviolet light source, and wherein such surface of the catalytic target structure comprises catalytic surface area for contact with the ultraviolet light from the ultraviolet light source.

6. The photohydroionization cell of claim 5, wherein the catalytic target structure comprises a total surface area that includes said catalytic surface area for contact with ultraviolet light from the ultraviolet light source, and said plurality of holes comprise between 0% and 95% of the total surface area.

7. The photohydroionization cell of claim 1, further comprising: a fiber optic cable with a first end oriented to receive light emitted from the ultraviolet light source, and a second end configured to provide an output light signal indicative of the operating status of the photohydroionization cell.

8. The photohydroionization cell of claim 7, further comprising: U.V. light filter configured to substantially filter U.V. light, while passing visible light that is visible by a person, the fiber optic cable cooperatively operating with the U.V. light filter to provide the visible light as the output light signal from the second end of the fiber optic cable.

9. The photohydroionization cell of claim 8, wherein the U.V. light filter comprises at least one of a U.V. filter, and U.V. filtering material in the fiber optic cable.

10. The photohydroionization cell of claim 1, further comprising: a protective barrier substantially encasing the ultraviolet light source, the protective barrier being substantially transparent to UV light for substantially passing UV light emitted from the UV light source at least within the UV light range in the 100 nm to 300 nm range while at the same time insulating the encased UV light source from external temperature.

11. The photohydroionization cell of claim 10, wherein the protective barrier comprises at least one of a protective coating and a tube that substantially encases the UV light source.

12. The photohydroionization cell of claim 11, wherein the protective barrier comprises a fluorocarbon protective barrier coating.

13. The photohydroionization cell of claim 11, wherein the protective barrier comprises quartz material.

14. The photohydroionization cell of claim 11, wherein the protective barrier comprises an anti-fouling external surface that substantially encases the UV light source to deter debris and other contaminants from contacting and adhering to the external surface encasing the UV light source while substantially passing UV light emitted from the UV light source at least within the UV light range in the 100 nm to 300 nm range.

15. The photohydroionization cell of claim 11, wherein the protective barrier is configured to provide a containment barrier in the event that the UV light source is broken.

16. The photohydroionization cell of claim 1, wherein a plurality of the plurality of holes are arranged in rows that extend along each of the apexes formed by the panels of the catalytic target structure.

17. A system for the formation of advanced oxidation product, the system comprising:
at least one ultraviolet light source for emitting broad spectrum ultraviolet light in the 100 nm to 300 nm range;
at least one single layer catalytic target structure mechanically coupled to and substantially surrounding the at least one ultraviolet light source, the catalytic target structure including:
a surface for contact by ultraviolet light from the at least one ultraviolet light source that, after contact with ultraviolet light, reacts with hydrate at the surface to form advanced oxidation product, the catalytic target structure having a repeating V-shaped geometry comprising a plurality of V-shaped pleatings that generally surround a circumference of the ultraviolet light source, the plurality of V-shaped pleatings including: (i) apexes formed by panels of the catalytic target structure that converge to point away from the ultraviolet light source and (ii) tips formed by panels of the catalytic target structure that converge and point towards the ultraviolet light energy source; and
a plurality of holes configured to allow passage of both surrounding gases and a portion of the ultraviolet light through the target structure, wherein the holes are arranged in rows that extend linearly in a longitudinal direction along the length of the panels that form the apexes and the tips of the plurality of V-shaped pleatings; and
a fiber optic cable, mechanically coupled with each of the at least one ultraviolet light source, the fiber optic cable including: a first end oriented to receive light emitted from respective each of the ultraviolet light source, and a second end configured to provide an output light signal indicative of the operating status of the system.

18. The system of claim 17, wherein the holes are circular.

19. The system for the formation of advanced oxidation product of claim 17, further comprising: U.V. light filter configured to substantially filter U.V. light, while passing visible light that is visible by a person, the fiber optic cable cooperatively operating with the U.V. light filter to provide the visible light as the output light signal from the second end of the fiber optic signal.

20. The system for the formation of advanced oxidation product of claim 17, further comprising: an adjustable power supply, electrically coupled to the at least one ultraviolet light source, for providing an adjustable electrical power signal thereto.

21. The system for the formation of advanced oxidation product of claim 17, further comprising: a UV Photo Detector, optically coupled with the second end of the fiber optic cable, and configured to provide an output signal indicative of an operational status of the at least one ultraviolet light source.

22. The system for the formation of advanced oxidation product of claim 21, further comprising:
an adjustable power supply, electrically coupled to the at least one ultraviolet light source, and configured to provide an adjustable electrical power signal thereto; and
a controller, electrically coupled with the adjustable power supply and the UV Photo Detector, configured to, in response to receiving an output data signal from the UV Photo Detector indicative of an operational status of the at least one ultraviolet light source, control the adjustable power supply for providing the adjustable electrical power signal to the at least one ultraviolet light source.

23. The system for the formation of advanced oxidation product of claim 22, further comprising: information means, coupled with the controller, configured to, in response to receiving an output data signal from the UV Photo Detector indicative of an operational status of the at least one ultraviolet light source, send an information/alert signal to a user/operator/technical personnel associated with the system.

24. The system for the formation of advanced oxidation product of claim 17, wherein a plurality of the plurality of holes are arranged in rows that extend along each of the apexes formed by the panels of the catalytic target structure.

* * * * *